United States Patent [19]

Ellis

[11] Patent Number: 5,006,510

[45] Date of Patent: Apr. 9, 1991

[54] METHOD FOR RELIEVING CHRONIC PAIN WITH A SOMATOSTATIN ANALOG COMPOSITION

[76] Inventor: Wladislaw V. Ellis, 2445 Carleton St., Berkeley, Calif. 94704

[21] Appl. No.: 368,660

[22] Filed: Jun. 20, 1989

[51] Int. Cl.$^5$ .............................................. A61K 37/02
[52] U.S. Cl. ...................................................... 514/16
[58] Field of Search ........................ 514/16, 947, 936; 530/328

[56] References Cited

U.S. PATENT DOCUMENTS

| | | | |
|---|---|---|---|
| 3,981,996 | 9/1976 | Leigh | 424/243 |
| 4,091,090 | 5/1978 | Tibor | 514/947 |
| 4,395,403 | 6/1983 | Bauer et al. | |
| 4,496,543 | 1/1985 | Bauer et al. | 514/16 |

FOREIGN PATENT DOCUMENTS

| | | | |
|---|---|---|---|
| 0255224 | 2/1988 | European Pat. Off. | 514/11 |
| 2193891A | 2/1988 | United Kingdom | |

OTHER PUBLICATIONS

Weber et al., *Surgery*, vol. 102(6), pp. 974–981.
M. Matucci-Cerinic, M.D. et al., "Somatostatin Treatment of Psoriatic Arthritis", Jan.–Feb. 1988, pp. 56–58, *International Journal of Dermatology*, vol. 27, No. 1.
Sandostatin ® octreotide acetate/SANDOZ Injection—Product insert, pp. 1–2, Columns 1–4, 1989 Sandoz Pharmaceuticals Corporation.

*Primary Examiner*—Lester L. Lee
*Assistant Examiner*—Stephen B. Maebius
*Attorney, Agent, or Firm*—Majestic, Parsons, Siebert & Hsue

[57] ABSTRACT

A particularly preferred peptide has the amino acid sequence (D)Phe-Cys-Phe-(D)Trp-Lys-Thr-Cys-Thr-ol and is combined with a carrier effective to promote passage of the peptide through a patient's skin for an antinociceptive composition useful for relieving pain in a patient experiencing burning pain or hyperesthesia. Topical application of the composition has been found dramatically to reduce such pain in most individuals treated for periods of from about 5–24 hours, and continued control of the pain can be had by daily doses.

6 Claims, No Drawings

METHOD FOR RELIEVING CHRONIC PAIN WITH A SOMATOSTATIN ANALOG COMPOSITION

FIELD OF THE INVENTION

The present invention relates to relief of pain, particularly chronic pain such as experienced as burning or hyperesthesia, with a non-opiate composition, and more particularly relates to a method for relieving pain with a somatostatin analog composition that can be topically administered.

BACKGROUND OF THE INVENTION

The treatment of chronic pain has proven notoriously difficult. Patients experiencing causalgia, sympathetic dystrophy, phantom-limb syndrome, denervation or herpetic pain are generally resistant to opiates in the sense that opiates will obtund the pain but will not significantly change the experience of the patient's pain.

Peptides have been used in attempts to treat such syndromes with little, if any, success. For example, substance P has been implicated in the pathogenesis of chronic pain such as neurogenic edema and causes significant pain of a burning and aching nature when injected subcutaneously. Somatostatin does exert modulatory effects on substance P (as well as a wide variety of other growth factors) but is very short-lived.

Psoriatic arthritis has been reported as possibly treatable with somatostatin by slow intravenous infusion; however, the side effects appear to be such that use of this drug should be limited to psoriatic patients with polyarthritis or with severe cutaneous involvement. Matucci-Cernic et al., *Intl. J. Dermatology*, 27, pp. 56–58 (1988).

Recently, a longer acting analog of somatostatin has been synthesized with eight amino acids. This peptide (also termed "octreotide") and its analogs exhibit GH (growth hormone) secretion-inhibiting activity as indicated, for example, by depression of serum GH levels in rats and described by U.S. Pat. No. 4,395,403, issued Jul. 26, 1983, inventors Bauer et al. This patent describes use of these peptides in treating gastrointestinal disorders or excess GH-secretion.

British Patent No. 2,193,891, published Feb. 24, 1988, inventors Azria et al. discloses nasal octreotide compositions for the purposes of treating disorders with an etiology associated with excess GH-secretion or gastrointestinal disorders. The nasal compositions include the octreotide and a non-ionic absorption promoter, such as various surfactants, for promoting absorption of the nasal mucosa.

Webber et al., *Surgery*, 102, pp. 974–981 (1987) describes studies with octreotide combined with two penetrant enhancers—dimethylsulfoxide or N-decylmethylsulfoxide. Particular amounts were topically applied to samples of skin from human cadavers and hairless mice for the potential use in treating endocrine disorders and insulin-dependent diabetes mellitus. The test data indicated very slow transdermal passage of the octreotide when combined with dimethylsulfoxide and compared with the octreotide in N-decylmethylsulfoxide. However, the authors concluded that the octreotide permeates both human and mouse skin when applied topically with N-decylmethylsulfoxide.

SUMMARY OF THE INVENTION

It is an object of the present invention to relieve pain in a patient experiencing burning pain or hyperesthesia through the administration of an antinociceptive composition that is readily administered, preferably by the patient herself, in amounts effective to relieve the pain without resort to opiates.

In one aspect of the present invention, a therapeutic method for relieving pain comprises topically administering an antinociceptive composition in an amount effective to relieve pain in a patient experiencing burning pain or hyperesthesia. The antinociceptive composition of the invention includes a peptide having the amino acid sequence

(D)Phe-Cys-Phe-(D)Trp-Lys-Thr-Cys-Thr-ol or an analog thereof, or a pharmaceutically acceptable acid addition salt or complex thereof, and a carrier effective to promote the passage of the peptide through the patient's skin.

In another aspect of the present invention, a therapeutic composition comprising the just-described peptide in solution, with the solution containing at least about 50 wt. % dimethylsulfoxide, is provided and preferably the peptide is in an amount from about 0.5 μg/ml to about 2 μg/ml and includes a minor amount of urea.

Practice of the inventive method has been found dramatically to reduce burning pain, as well as hyperesthesia, in most individuals treated for periods of from about 5–24 hours, and continued control of the pain can be had by daily doses.

DETAILED DESCRIPTION OF THE PREFERRED EMBODIMENTS

This invention will be better understood with reference to the following definitions.

Hyperesthesia. By "hyperesthesia" is meant a morbid response to normal sensory stimuli, which are perceived as extremely painful.

Burning pain (causalgia). By "burning pain" or "causalgia" is meant a pathological response to nerve injury, commonly severely disabling and previously with no known cure.

Both hyperesthesia and burning pain are dehabilitating and arise in some individuals following a wide spectrum of injuries to nerve tissue (e.g., high velocity injuries; surgery; viral infections, such as herpes; trauma to peripheral nerves; chronic metabolic disease).

By "antinociceptive" is meant "anti-pain".

Compositions of the invention include a peptide having the amino acid sequence

(D)Phe-Cys-Phe-(D)Trp-Lys-Thr-Cys-Thr-ol or an analog thereof, or a pharmaceutically acceptable acid addition salt or complex thereof. By "Thr-ol" is meant the Threoninol residue. More broadly, this peptide and its analogs are of Formula I.

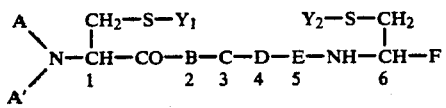

wherein

A is $C_{1-12}$ alkyl, $C_{7-10}$ phenylalkyl or a group of formula RCO—, whereby
  (i) R is hydrogen, $C_{1-11}$ alkyl, phenyl or $C_{7-10}$ phenylalkyl, or
  (ii) RCO— is
    (a) an L- or D-phenylalanine residue optionally ring-substituted by halogen, $NO_2$, $NH_2$, OH, $C_{1-3}$ alkyl and/or $C_{1-3}$ alkoxy
    (b) —Asn— or the residue of a natural α-amino acid having a hydrocarbyl side chain other than defined under (a) above or of a corresponding D-amino acid, or
    (c) a dipeptide residue in which the individual amino acid residues are the same or different and are selected from those defined under (a) and/or (b) above, the α-amino group of amino acid residues (a) and (b) and the N-terminal amino group of dipeptide residues (c) being optionally mono- or di-$C_{1-12}$ alkylated, A′ is hydrogen or, when A is $C_{1-12}$ alkyl or $C_{7-10}$ phenylalkyl, also $C_{1-12}$ alkyl or $C_{7-10}$ phenylalkyl, B is —Phe— optionally ring-substituted by halogen, $NO_2$, $NH_2$, OH, $C_{1-3}$ alkyl and/or $C_{1-3}$ alkoxy, C is —(L)— or —(D)—Trp— optionally α-N-methylated and optionally benzene-ring-substituted by halogen, $NO_2$, $NH_2$, OH, $C_{1-3}$ alkyl and/or $C_{1-3}$ alkoxy, D is —Lys— optionally α-N-methylated and optionally ε-N-$C_{1-3}$ alkylated, E is —Thr— or —Ala— each in (D)- or (L)- form and each being optionally α-N-methylated, F is a group of formula

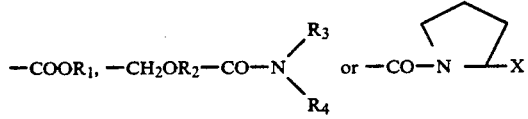

wherein $R_1$ is hydrogen or $C_{1-3}$ alkyl, $R_2$ is hydrogen or the residue of a physiologically acceptable, physiologically hydrolysable ester, $R_3$ is hydrogen, $C_{1-3}$ alkyl phenyl, benzyl or $C_{9-10}$ phenylalkyl or, when $R_3$ is hydrogen or methyl, also a group of formula —CH($R_5$)—X wherein $R_5$ is hydrogen, —$(CH_2)_2$—OH, —$(CH_2)_3$—OH, —$CH_2$—OH, —CH($CH_3$)—OH, isobutyl or benzyl and X is a group of formula

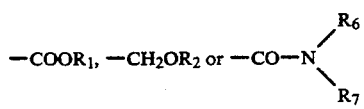

wherein $R_1$ and $R_2$ have the meanings given above, $R_6$ is hydrogen or $C_{1-3}$ alkyl and $R_7$ is hydrogen, $C_{1-3}$ alkyl, phenyl or $C_{7-10}$ phenylalkyl, the group —CH($R_5$)—X having the D- or L-configuration, and $Y_1$ and $Y_2$ are each hydrogen or together represent a direct bond,
  whereby the residues in the 1- and 6-position each independently have the L- or D-configuration,
  with the proviso (i) that D- and/or L-cysteine residues are present at the 1- and 6-positions only, and
  (ii) that when $R_5$ is benzyl, X is a group of formula

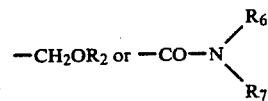

or a group of formula —$COOR_1$, wherein $R_1$ is $C_{1-3}$ alkyl, or a pharmaceutically acceptable acid addition salt or complex thereof.

Acid addition salts of the Formula I peptide may be formed with organic acids, polymeric acids and inorganic acids. Acid addition salt forms include the hydrochlorides and acetates. Complexes are compounds of Formula I formed on addition of inorganic substances such as inorganic salts of hydroxides (e.g., calcium and zinc salts and/or addition of polymeric organic substances).

A particularly preferred peptide for practice of the invention has the amino acid sequence

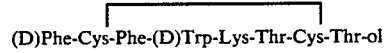

and is in the acetate salt form. The peptide and analog are more fully described by U.S. Pat. No. 4,395,403, incorporated herein by reference.

Compositions of the invention for practice of the therapeutic method of relieving pain also include a carrier effective to promote the passage of the peptide through the patient's skin. A preferred carrier is dimethylsulfoxide in an amount of at least about 50 wt. % of the solution in which the peptide is present, more particularly in an amount from about 50 wt. % to about 80 wt. %.

Additional agents may be present in the peptide solution, such as an odor masking agent for the dimethylsulfoxide and/or an agent to reduce skin irritation causable in some patients by application of the antinociceptic composition. Urea fulfills both an odor masking and skin irritation reduction role, and is a preferred additional component in compositions of the invention. When compositions of the invention include urea, then it is preferably present in an amount from about 50 wt. % to about 20 wt. %.

Therapeutic compositions of the invention preferably are prepared with peptide in an amount of from about 0.5 μg/ml to about 2 μg/ml, and about 0.2 μg to about 2 μg of the peptide are administered daily. Topical administration may be effected on the skin immediately covering the area of pain.

EXPERIMENTAL

Commercially available octreotide acetate (from Sandoz under the designation "Sandostatin") was added to a 75% solution of DMSO (Mallincrodt) to a concentration of 1 μg/ml octreotide in the final solution. Informed consent was obtained from patients afflicted with chronic, disabling, burning pain and the experimental solution was topically applied to them.

The dramatic reduction of burning pain as well as hyperesthesia in the initial individuals treated prompted the use of this composition in other individuals with complaints of similar pain.

The clinical effectiveness of this treatment resulted in a double bind study to establish the validity of this effect.

Experimental Population

There were 15 males and 3 females in the initial study. The age ranged from 24 to 65. The majority of the patients had been afflicted with severe burning pain and hyperesthesia for longer than one year and many of them had multiple other disorders.

Results

Topical self-administration of 1 ml twice a day for one week resulted in no appreciable local or systemic changes except for the characteristic localized rubor and odor of DMSO. Application of the experimental solution to a self-administered small incision resulted in immediate intensification of that pain lasting for approximately one minute and presumed due to the DMSO, with a subsequent continued ache but a progressive diminution of the hyperesthesia characteristic of injury to non-existent levels within twenty minutes of the application. A control incision continued appreciably hyperesthetic for approximately 5 hours.

The first patient tested had a one-year history of post-carpal tunnel surgery causalgia in the right hand. She experienced severe burning pain at the incision site with hyperesthesia of a painful nature throughout her right arm, shoulder and neck. Local application of 0.2 ml of the inventive composition onto her scar resulted in the complete disappearance of her burning pain and hyperesthesia within a twenty minute period. She continued to experience a much less severe but constant dull aching pain at the scar with continued dull arm, shoulder and neck pain.

The second patient was the victim of a crushing industrial injury to his left shoulder and rib cage with an eight-week history of constant and worsening burning pain spread throughout his upper left rib cage and the left shoulder. Application of 0.2 ml daily for three days to the affected area resulted in the complete disappearance and continued absence of the previously disabling burning pain.

The solution was then tried in two middle-aged brothers suffering from multiple organ diseases with severe and chronically painful musculoskeletal disorders and a seven-year history of hyperesthesia. Both reported dramatic lessening of these symptoms with local application.

Trials in seven other patients resulted in overwhelmingly positive responses in all but one case. The exception decided that the temporary benefit (2-3 hours of decreased pain) that the solution offered her was decreased by the burning produced by the DMSO itself.

In order to deal with this issue, 20 wt. % urea was added to the inventive composition, which resulted in a marked decrease in complaints of burning or odorousness. The patients reported identical therapeutic effect, and an overwhelming preference for the urea based composition.

At this point, a double-blind study was performed with eight patients experiencing deep burning pain. Patients were issued randomly labeled, identical bottles which contained either 75% DMSO alone (four patients) or 75% DMSO with octreotide 1 µg/ml (the other four patients). Neither the investigator nor the patients knew if the active ingredient (the octreotide) was in the bottle. All four patients treated with the octreotide reported relief while none of the four treated with control did so. Of interest is that the majority of the patients treated with octreotide also reported an improvement in mood. Whether the octreotide has a direct normalizing effect on mood or whether the mood improvement is due entirely to the lessened pain still remains to be determined.

In all the patients treated with the inventive composition, the octreotide removed all burning pain and hyperesthesia. The relief of other qualitatively different pains was highly variable from individual to individual with some reporting total pain relief for 8-24 hours while others continue to experience significant disability from "deep aching" pain.

Octreotide is thus believed the first peptide to have shown a clear-cut antinociceptive effect in humans. Topical application of octreotide at concentration of 1 µg/ml using 75% DMSO as carrier eliminates burning pain as well as hyperesthesia for between 5-24 hours at total doses of less than 1 µg per day. This effect has been dramatically demonstrated in a large number of individuals who have been severely disabled because of causalgia, sympathetic dystrophy, denervation pain, radicular pain as well as other disorders, all of which have responded dramatically to this peptide.

It is to be understood that while the invention has been described in conjunction with preferred specific embodiments, the foregoing description as well as the examples are intended to illustrate and not limit the scope of the invention, which is defined by the scope of the appended claims. Other aspects, advantages and modifications within the scope of the invention will be apparent to those skilled in the art to which the invention pertains.

It is claimed:

1. A therapeutic method for relieving burning pain or hyperesthesia at the site of topical administration comprising:

topically administering an antinociceptive composition to relieve pain in a patient experiencing burning pain or hyperesthesia, the antinociceptive composition including a peptide having the amino acid sequence

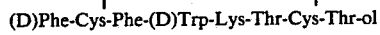

(D)Phe-Cys-Phe-(D)Trp-Lys-Thr-Cys-Thr-ol or a pharmaceutically acceptable acid addition salt or complex thereof, wherein the antinociceptive composition is a solution having from about 0.2 µg to about 2 µg peptide per unit dose and wherein the composition includes dimethyl sulfoxide that serves as a carrier to promote the passage of the peptide through the patient's skin.

2. The method as in claim 1 further comprising an odor masking agent for the dimethyl sulfoxide.

3. The method as in claim 1 further comprising an agent to reduce skin irritation causable by application of the antinociceptive composition.

4. The method as in claim 1 wherein about 0.2 µg to about 2 µg of the peptide are administered daily.

5. The method as in claim 1 wherein the dimethyl sulfoxide comprises at least about 50 wt. % of said antinociceptive composition.

6. The method as in either claim 2, 3, 4, or 5 wherein the antinociceptive composition includes urea.

* * * * *